United States Patent [19]

Tull et al.

[11] 4,294,988

[45] Oct. 13, 1981

[54] METHOD OF PREPARING 2,4-DIFLUOROANILINE

[75] Inventors: Roger J. Tull, Metuchen; Leonard M. Weinstock, Bellemead; Ichiro Shinkai, Westfield, all of N.J.

[73] Assignee: Merck & Co., Inc., Rahway, N.J.

[21] Appl. No.: 847,187

[22] Filed: Oct. 31, 1977

[51] Int. Cl.³ .............................................. C07C 85/11
[52] U.S. Cl. .................................... 564/417; 260/689; 260/694; 564/412; 568/938
[58] Field of Search ................. 260/580, 646; 564/417

[56] References Cited

FOREIGN PATENT DOCUMENTS 960046  6/1964  United Kingdom ................ 260/580

OTHER PUBLICATIONS

Finger et al., "JACS", vol. 78, pp. 6034–14 6037 (1956).
Kraus et al., "Catal. Proc. Int. Congr.", 5th, pp. 1073–1084 (1972).

Primary Examiner—John Doll
Attorney, Agent, or Firm—Theresa Y. Cheng; Raymond M. Speer; Mario A. Monaco

[57] ABSTRACT

A method of preparing 2,4-difluoroaniline by reacting 2,4,5-trichloronitrobenzene with a fluorinating agent to form 2,4-difluoro-5-chloronitrobenzene which is then hydrogenated with hydrogen in the presence of a catalyst to form 2,4-difluoroaniline.

8 Claims, No Drawings

METHOD OF PREPARING 2,4-DIFLUOROANILINE

BACKGROUND OF THE INVENTION (1) Field of the Invention

A method of preparing 2,4-difluoroaniline.

(2) Description of the Prior Art

G. C. Finger and C. W. Kruse, in *JACS*, 78, 6034 (1956), have described fluorination of 2,3,4-trichloro nitrobenzene with potassium fluoride in dimethylsulfoxide, to form 1,3-difluoro-2-chloro-6-nitrobenzene, but in low yield. Finger et al., in *JACS*, 81, 94 (1959), have described fluorination of 3,4,5-trichloronitro-benzene with potassium fluoride in dimethylformamide, to form 3,5-dichloro-4-fluoronitrobenzene in fairly high yield. However, the art does not suggest the specific fluorination by chlorine replacement to form 2,4-difluoro-5-chloronitrobenzene achieved with the method of the present invention.

Hydrogenolysis of various halobenzenes with hydrogen over palladium-carbon by M. Kraus and V. Bazant, reported in *Catal., Proc. Int. Congr.*, 5th, 1972, 2, 1073-84, determined that reactivity decrease occurred in the order Br, Cl, F. And R. E. Florin et al., in *J. Res. Natl. Bur. St.*, 62, 119 (1959) found that hydrogenation with hydrogen over palladium-carbon of 2, 3, 4, 5-tetrafluorochlorobenzene formed 1,2,3,4-tetrafluorobenzene in fairly high yield. However, when catalytic reduction over palladium black of aromatic fluoro chloro nitro compounds was carried out by N. Vorozhtsov et al., reported in *Zhur. Obshchei Khim.*, 31, 1229-32 (1961), it was found that 2,4-difluoro-5-chloroaniline was formed. Thus, the art does not suggest the catalytic reduction of the method of the present invention whereby the nitro group is reduced to amine and the chlorine substituent is displaced without affecting the fluorine substituents, in a very specific manner.

A commonly employed method in the art currently for preparing 2,4-difluoroaniline is one which prepares 2,4-dichlorobenzene as an intermediate and uses benzene as a starting material. However, this process requires use of AlCl₃ catalyst, an expensive material, as well as fractional distillation. The intermediate is then nitrated, and fluorine replacement and reduction produces 2,4-difluoroaniline. The reactions of this conventional method may be illustrated as follows:

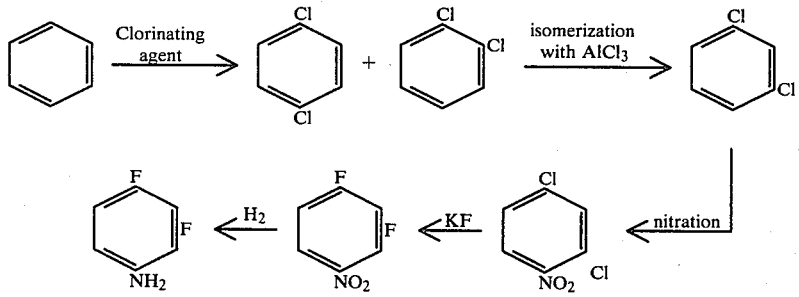

The method of the present invention avoids the expensive isomerization step of the above process by employing trichlorobenzene, an inexpensive starting material, with specific chlorine removal at the time of fluorine replacement.

SUMMARY OF THE INVENTION

The method of the present invention is concerned with preparation of 2,4-difluoroaniline. More particularly, the method of the present invention comprises two steps characterized by high specificity whereby preparation of 2,4-difluoroaniline is greatly simplified and improved. The first step involves fluorination of 2,4,5-trichloronitrobenzene whereby two of the chlorine substituents are replaced by fluorine in a specific manner to form 2,4-difluoro-5-chloronitrobenzene. The second step involves hydrogenation of the 2,4-difluoro-5-chloronitrobenzene whereby the nitro substituent is reduced to amine, the chlorine substituent is displaced to form HCl, and the two fluorine substituents remain unaffected. The hydrogenation step is, thus, quite specific.

The method of the present invention, comprising basically two steps, but three separate reactions, may be schematically represented as follows:

Step 1. - Fluorination of 2,4,5-trichloronitrobenzene

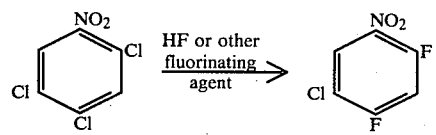

Step 2. - Hydrogenation of 2,4-difluoro-5-chloronitrobenzene

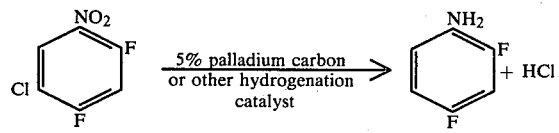

The starting material for the method of the present invention may be 1,2,4-trichlorobenzene, an inexpensive material. This material must then be nitrated to prepare 2,4,5-trichloronitrobenzene. However, it is preferred to employ 2,4,5-trichloronitrobenzene as a starting material since it is fairly readily available and relatively inexpensive.

The fluorination step of the method of the present invention is carried out under anhydrous conditions using a fluorinating agent selected from the group consisting of NaF, KF, CsF, and $C_{1-4}$ alkyl quaternary ammonium fluoride, and mixtures thereof. KF is preferred as the fluorinating agent. Since the presence of water slows the fluorination considerably, the reaction conditions must be substantially anhydrous, although trace amounts of water can be tolerated. Anhydrous conditions are maintained by employing a solvent reaction medium. The solvent reaction medium should be dipolar and aprotic. A number of solvents are suitable for this purpose, for example, one selected from dimethylsulfoxide, tetramethylsulfone, dimethylformamide, dimethylacetamide, tetramethylurea, dimethylsulfone, and hexamethylphosphoramide. A molar excess of the fluorinating agent, e.g., potassium fluoride, is used, usually of at least five-fold in amount. The fluorination reaction is carried out at elevated temperatures of from about 75° to about 225° C., preferably of from about 125° to about 175° C., and for a period of time ranging from about 3 to about 30 hours, usually from 8 to about 20 hours.

The 2,4-difluoro-5-chloronitrobenzene formed by the fluorination step is next subjected to the catalytic hydrogenation step of the method of the present invention. The catalyst employed is preferably a 5% palladium carbon catalyst. The catalyst is an activated carbon substrate impregnated with 5% by weight of palladium. The manner of impregnation is not critical and palladium carbon catalysts prepared by various conventional processes are suitable. A 5% palladium carbon catalyst available from Engelhard Industries, Inc. has been found especially suitable. A 10% palladium carbon catalyst has been found to give results essentially similar to those obtained with the 5% palladium catalyst. Other catalysts which may be employed are $Ni/Cr_2O_3$ or Raney nickel catalysts, preferably on an activated carbon substrate. The amount of catalyst employed will usually be from about 5% to about 25% by weight of the amount of 2,4-difluoro-5-chloronitrobenzene starting material. The catalyst material and starting material are added to a suitable solvent, for example, methanol or higher alkanol, or aqueous mixtures of these, together with sodium acetate or other mild base to neutralize the HCl formed during the reaction. Hydrogen is then bubbled through the reaction solution by means of suitable apparatus, for example, a Parr hydrogenater. The reaction solution is stirred or shaken while hydrogen is passed through the solution.

The reaction solution is initially maintained at a temperature of from about 0° to about 100° C. However, reduction of the nitrate group is exothermic and cooling may be required if the apparatus employed does not permit dissipation of the heat generated. Otherwise, by starting at a sufficiently low temperature, it is possible to run the total hydrogenation process straight through without addition or extraction of any heat. The chlorine removal portion of the hydrogenation process requires temperatures between about 20° to 100° C. Thus, it is possible, but not necessary, to carry out the hydrogenation process in essentially two stages: nitro group reduction followed by chlorine removal.

The hydrogen pressure during hydrogenation is usually maintained between about 3 and 10 atmospheres, most usually about 3 atmospheres or 40 psig. Stoichiometrically, four moles of hydrogen are required for hydrogenation of 2,4-difluoro-5-chloronitrobenzene. As a practical matter, hydrogen is passed through the reaction solution until the reaction is complete, since all the hydrogen which is required for the hydrogenation reaction will be consumed, and any excess or additional amounts will have no adverse consequences. Thus, the time required for the hydrogenation step will depend on a number of factors, including hydrogen pressure and temperature of the reaction solution. Usually, hydrogenation will be complete in from about 1 to about 5 hours.

Typically, the hydrogenation may be carried out as follows: after at least about three moles of hydrogen have been passed through the solution, the solution is heated to a temperature of from 50° to 70° C. and an additional at least two moles of hydrogen are passed through the solution.

EXAMPLE 1

Step 1: Preparation of 2,4-difluoro-5-chloronitrobenze: Fluorination of 2,4,5-trichloronitrobenzene 5 g. ($2.208 \times 10^{-2}$ mole) of 2,4,5-trichloronitrobenzene was added to 30 ml. of tetramethyl sulfone together with 6.4 g. ($1.102 \times 10^1$ mole) of anhydrous potassium fluoride. The reaction mixture was then heated at 170°–180° C. for 19 hours. The reaction mixture was then subjected to steam distillation and the distillate of about 150 ml. was extracted with ether five times at 20 ml. per extraction. The extract was dried over $Na_2SO_4$ to give 1.56 g. of a yellow oil. The residue after extraction was treated with 150 ml. water and then extracted with ether five times at 40 ml. per extraction. The extract was dried over $Na_2SO_4$ to give a yellow oil. The yellow oil was purified on a column of silica gel ($3 \times 25$ cm.) by first eluting with 5% $CHCl_3$/n-hexane (1:9) to yield 310 mg. of 2,4,5-trichloronitrobenzene starting material, and then 10% $CHCl_3$/n-hexane (1:9) to yield 670 mg. of 2,4,difluoro-5-chloronitrobenzene. Both results were confirmed by NMR and TLC. The total yield of 2,4-difluoro-5-chloronirobenzene was 2.23 g. or 52%.

Step 2: Preparation of 2,4-difluoroaniline: Hydrogenation of 2,4-difluoro-5-chloronitrobenzene 1.0 g. ($5.17 \times 10^{-3}$ mole) of 2,4-difluoro-5-chloronitrobenzene, together with 450 mg. ($5.49 \times 10^{31}$ $^3$ mole) of sodium acetate, was added to 30 ml. of methanol. 100 mg. of a 5% palladium-carbon catalyst was added and hydrogen was then passed through the reaction mixture for a period of 3 hours in a total amount of 22 lbs (3 moles). The reaction mixture was then heated to 60° C. and hydrogen was allowed to pass through the mixture for the next 20 hours, in a total amount of 11.5 lbs. The reaction mixture was then filtered to remove the catalyst material and sodium acetate. The final product was separated by evaporation of the solvent under vacuum, followed by water washing of the product. The product was then introduced into an insoluble solvent, followed by distillation. The yield was approximately 70%.

EXAMPLE 2

Preparation of 2,4-difluoroaniline: Hydrogenation of 2,4-difluoro-5-chloronitrobenzene 2.0 g. ($1.03 \times 10^{-2}$ mole) of 2,4-difluoro-5-chloronitrobenzene, together with 900 mg. ($1.1 \times 10^{-2}$ mole) of sodium acetate, and 0.2 g. of 5% palladium carbon catalyst, was added to 30 ml. of methanol. 40 lbs of hydrogen was passed through the reaction mixture for 3 hours, after which it was heated to 60° C. During the following 6 hours and 14 minutes an additional 12 lbs of hydrogen was passed through the reaction mixture. The catalyst and sodium acetate were removed by filtration and washed with 10 ml. of methanol. The reaction mixture was then concentrated to about 5 ml. and poured into 40 ml. of a 5% $Na_2CO_3$ solution. The solution was extracted with chloroform three times at 20 ml. per extract. The extract was dried over $Na_2SO_4$. The solvent was evaporated under reduced pressure and the residue was purified by vacuum distillation. The yield of final product was 640 mg., which was 48%.

The 2,4-difluoroaniline prepared by the method of the present invention is a well known starting material and intermediate for a number of organic syntheses. See *The Merck Index*, ninth edition, pg. 415 (1976). Especially, the 2,4-difluoroaniline prepared by the method of the present invention is a useful starting material for preparation of 2′, 4′-difluoro-4-hydroxy-[1,1′-biphenyl]-3-carboxylic acid, a valuable anti-inflammatory and analgesic agent for therapeutic use.

What is claimed is:

1. A method of preparing 2,4-difluoroaniline comprising the steps of
   (a) reacting 2,4,5-trichloronitrobenzene under anhydrous conditions with a fluorinating agent selected from NaF, KF, CsF, $C_{1-4}$ alkyl quaternary ammonium fluoride, and mixtures thereof, to form 2,4-difluoro-5-chloronitrobenzene; and
   (b) hydrogenating the 2,4-difluoro-5-chloronitrobenzene with hydrogen in the presence of a catalyst to form 2,4-difluoroaniline.

2. The method of claim 1 wherein the anhydrous conditions comprise employing as a solvent reaction medium a dipolar, aprotic solvent.

3. The method of claim 2 wherein the dipolar, aprotic solvent is selected from dimethylsulfoxide, tetramethylsulfone, dimethylformamide, dimethylacetamide, tetramethylurea, dimethylsulfone, and hexamethylphosphoramide.

4. The method of claim 1 wherein the fluorinating agent is KF.

5. The method of claim 1 wherein the catalyst is palladium impregnated activated carbon.

6. The method of claim 1 wherein the step of treatment with a fluorinating agent is carried out at a temperature of from about 75° to about 225° C., and for a period of time ranging from about 3 to about 30 hours.

7. The method of claim 1 wherein the step of hydrogenating is carried out at a temperature of from about 0° to about 100° C., and for a period of time ranging from about 1 to about 5 hours.

8. The method of claim 1 wherein during the step of hydrogenating the hydrogen is maintained at a pressure between about 3 and 10 atmospheres.

* * * * *